United States Patent
Whitehurst et al.

(10) Patent No.: US 8,320,600 B2
(45) Date of Patent: Nov. 27, 2012

(54) METHOD AND APPARATUS TO ENHANCE COMMUNICATION IN THE OPERATING ROOM

(75) Inventors: Todd K. Whitehurst, Valencia, CA (US); Rafael Carbunaru, Valley Village, CA (US); Kristen Jaax, Santa Clara, CA (US); James Makous, Santa Clarita, CA (US); Courtney Lane, Ventura, CA (US); Mark Pierre, Chicago, IL (US); Cliff Brainard, Valencia, CA (US); Charles Tilden Hagan, IV, Chapel Hill, NC (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 452 days.

(21) Appl. No.: 12/506,938

(22) Filed: Jul. 21, 2009

(65) Prior Publication Data

US 2011/0019858 A1 Jan. 27, 2011

(51) Int. Cl.
*H04R 11/04* (2006.01)

(52) U.S. Cl. ............. 381/361; 381/77; 381/79; 381/87; 381/301; 381/26; 600/546; 600/407; 600/559

(58) Field of Classification Search .............. 600/546, 600/407, 559; 381/361, 77, 79, 87, 301, 381/26; 340/539
See application file for complete search history.

(56) References Cited

U.S. PATENT DOCUMENTS

| | | | | |
|---|---|---|---|---|
| 3,869,584 A * | 3/1975 | Wilde | | 379/430 |
| 4,752,064 A * | 6/1988 | Voss | | 5/638 |
| 4,981,139 A | 1/1991 | Pfohl | | |
| 5,479,474 A * | 12/1995 | Schwartzman et al. | | 455/570 |
| 6,023,801 A * | 2/2000 | Lamm | | 5/636 |
| 6,405,165 B1 | 6/2002 | Blum et al. | | |
| 6,668,196 B1 * | 12/2003 | Villegas et al. | | 607/60 |
| 7,138,902 B2 | 11/2006 | Menard | | |
| 7,677,734 B2 * | 3/2010 | Wallace | | 353/18 |
| 2006/0053556 A1 * | 3/2006 | Piontek | | 5/637 |
| 2006/0286960 A1 * | 12/2006 | Goehler | | 455/403 |
| 2007/0208391 A1 | 9/2007 | Wahlstrand et al. | | |
| 2009/0093685 A1 * | 4/2009 | Vu et al. | | 600/300 |
| 2009/0147965 A1 * | 6/2009 | Kuo | | 381/71.6 |
| 2010/0257674 A1 * | 10/2010 | Beall et al. | | 5/630 |

FOREIGN PATENT DOCUMENTS

JP 2006-197267 * 7/2006

OTHER PUBLICATIONS

Emerson, Dan, Hopitals Wheels in Wireless Future, Minneapolis / St. Paul Business Journal, Mar. 8, 1999 (2 pages).
Schlegel, Robert et al., Electromagnetic Compatibility Study of the In-Vitro Interaction of Wireless Phones with Cardiac Pacemakers, Biomedical Intrumentation and Technology, 32(6): 645-55, 1998, Nov.-Dec.

* cited by examiner

*Primary Examiner* — Davetta W Goins
*Assistant Examiner* — Kuassi Ganmavo
(74) *Attorney, Agent, or Firm* — Vista IP Law Group LLP

(57) ABSTRACT

A communication system is provided for a patient featuring a cushion with an opening for receiving the face of the patient. The cushion includes a microphone for receiving audible signals from the patient and one or more speakers for delivering audible signals to the patient. The microphone and speaker(s) are integrated with the cushion to avoid interfering with the comfort of the patient. In one embodiment, the audible signals are delivered to and from the patient via a communication port. In another embodiment, the system includes a display device, so the patient may view parts of the patient's body on the device and then communicate with system operators through the microphone and speaker(s).

18 Claims, 2 Drawing Sheets

METHOD AND APPARATUS TO ENHANCE COMMUNICATION IN THE OPERATING ROOM

FIELD OF THE INVENTION

The present invention relates methods and apparatus to facilitate communication between a patient and medical personnel in an operating room.

BACKGROUND OF THE INVENTION

During numerous medical procedures, verbal feedback from the patient is often critical to the success of the operation. The patient's own nervous feedback system is often preferred over even the most complex monitoring technology. For example, in a procedure involving the treatment of migraine headaches, a lead electrode is inserted into the back of a patient's head to stimulate the occipital nerves. The patient, lying face down, is then required to give verbal feedback regarding the location of the paresthesia experienced from the stimulation. The lead can then be adjusted to stimulate different areas on or around the nerves until the patient reports successful stimulation. However, there is significant difficulty in comprehending the patient's speech while in this state.

Regarding communication in the operating room, the application of wireless technology has long been a topic of contention within the medical and communications fields, due to concerns about electromagnetic interference with medical equipment. For example, there has been particular concern among medical professionals about the electromagnetic signal from cell phones interfering with vital medical equipment such as heart pacemakers. Notably, however, a 2006 study of 8,296 tests runs involving variable cell phone broadcasters and pacemakers found that no interference occurred beyond 8.7 inches of the cell phones' position relative to the pacemakers, even with the oldest phone models running at their highest power. The study also reported 6 inches as the outside boundary of interference "for the overwhelming majority of pacemakers which exhibited interaction," with modern CDMA and PCS 1900 standard phones exhibiting only 2.8% and 0.6% interference rates, respectively, even within that distance. (Reference: *Electromagnetic compatibility study of the in-vitro interaction of wireless phones with cardiac pacemakers*, Schlegel, R. E., Grant, F. H., Raman, S., Reynolds, D., "Biomedical Instrumentation and Technology," 32(6):645-55, November-December 1998) Continuing advances in electromagnetic shielding standards as well as in low-power high-frequency wireless technology should eliminate interference incidents entirely in the near future.

With the perceived risk posed to vital medical equipment by wireless communication being thus diminished, there are opportunities to utilize wireless technology to benefit operating procedures. Thus, there is a need to provide a versatile system for wireless verbal communication between the patient and surgical staff for minimizing communication issues during stimulation device implant procedures and allowing patients to accurately guide their physicians, thus maximizing the benefits of electronic stimulation.

SUMMARY OF THE INVENTION

In accordance with one aspect of the present invention, a cushion-mounted patient communication system is provided. The system comprises a cushion with an opening for receiving the patient's face, a microphone in the cushion for receiving audible signals from the patient, and at least one speaker in the cushion for delivering audible signals from an operator, e.g., medical personnel, to the patient. In one embodiment, the system further includes a communication port for receiving the patient's audible signals from the microphone and delivering the operator's audible signals to the speaker. Different embodiments of the microphone include a bone-conductive microphone or a throat microphone. In another embodiment, the system further includes a display device that is integrated with the cushion and viewable by the patient. The display device is configured for displaying selected areas of the patient's body.

In accordance with a second aspect of the present invention, a method for a patient to communicate during a medical procedure is provided. The method includes positioning the patient's face in an opening surrounded by a cushion, wherein the cushion supports the patient's head. Audible signals are delivered from the patient into a microphone embedded in the cushion and then to a communication port. Audible signals are also delivered to the patient from the communication port through at least one speaker that is at least partially embedded in the cushion. In another embodiment, the method includes displaying selected parts of the patient's body at a display device integrated with the cushion, and may further include receiving commands from the communication port to display the selected parts of the patient's body at the display device.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
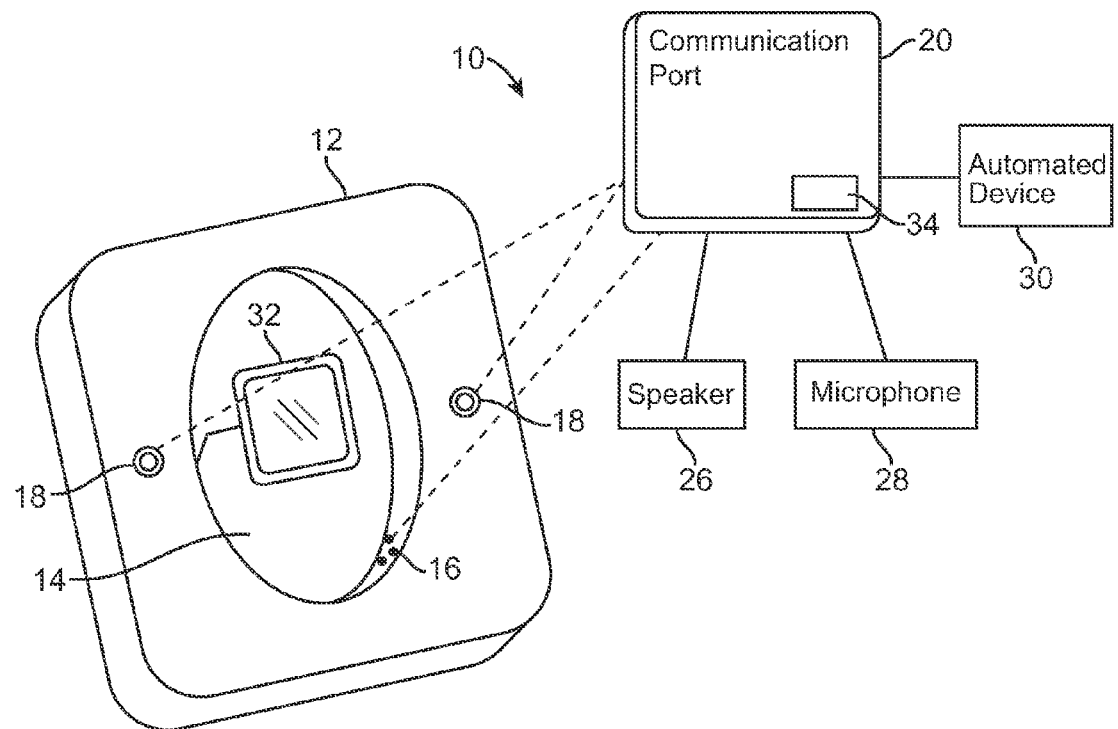
FIG. 1 is a plan view of one embodiment of a cushion-mounted patient communication system arranged in accordance with the present invention.

Turning first to FIG. 1, an exemplary communication system 10 constructed in accordance with one embodiment of the present inventions for facilitating communication during a medical procedure between a patient and medical or other personnel (e.g., physician, anesthesiologist, field clinical engineer (FCE), sales representative, nurse, radiologist, and supporting staff) is shown. Generally, the communication system 10 includes a cushion 12 with an opening 14 for receiving the patient's head. The cushion 12 may be integrated with, or somewhere be associated, with an operating table (not shown) on which the patient lies down. The cushion 12 also features a microphone 16 for receiving audible signals from the patient and one or more speakers 18 for delivering audible signals to the patient. A communication port 20 is configured to receive the patient's audible signals from the microphone 16 and to deliver audible signals from medical personnel or a device used in the procedure to the speakers 18 for the patient to hear.

The cushion 12 is configured to receive the patient's head, and in particular the patient's face, while promoting patient comfort. Thus, the patient may lie face-down during a medical procedure with minimal discomfort, while still being able to communicate with medical personnel. Preferably, the cushion 12 is attached to a chair or bed on which the patient is positioned. However, the cushion 12 may also be configured for placement wherever the patient or the medical personnel choose for suitable operation.

Figure 2:
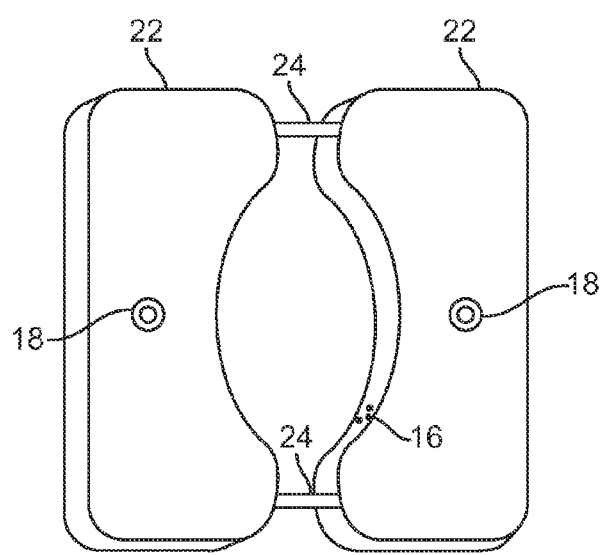
FIG. 2 is a perspective view of an alternative embodiment of a cushion used in the communication system of FIG. 1.

In the illustrated embodiment, the cushion 12 is square and the opening 14 is elliptical. However, the cushion 12 and the opening 14 may be configured in any shape suited to the patient and/or the medical procedure. For example, the cushion 12 may embody ring, horseshoe, or rectangular shapes, and the opening 14 may embody rectangular, circular, or tear-drop shapes. In another example, shown in FIG. 2, the cushion 12 includes two separate portions 22 joined by connecting elements 24 at opposite ends, with the opening 14 between the cushion portions 22. The width of the opening 14 is adjusted by sliding the cushion portions 22 along the connecting elements 24. The connecting elements 24 may also include locking elements (not shown) to lock the cushion portions 22 in position.

The cushion 12 is preferably filled with foam or other compressible material(s) and may further include a soft fabric cover added comfort and/or for wicking moisture from the patient's skin. Both the fabric of the cushion 12 and the cushion filling can be designed to meet particular specifications for a patient or medical procedure. For example, the fabric may be composed of an allergen-free material or a breathable mesh, and the filling may be a firm foam or a soft foam, as suited to the patient.

Referring back to FIG. 1, the microphone 16 is partially or completely embedded in the cushion 12 for receiving audible signals from the patient, for example voice communications, to be delivered to the communication port 20. In the illustrated embodiment, the microphone 16 is embedded in the cushion 12, such that a surface of the microphone 16 is flush with an external surface of the cushion 12, and is positioned to be adjacent the patient's mouth for receiving voice communications from the patient. In this manner, the microphone 16 does not interfere with the patient's face or the patient's comfort, while still being sufficiently close to the patient to receive audible signals from the patient. However, the microphone 16 can also be configured in any suitable manner that allows the microphone 16 to receive audible signals from the patient. For example, the microphone 16 may slightly protrude from the cushion 12 near the patient's mouth.

Figure 3:
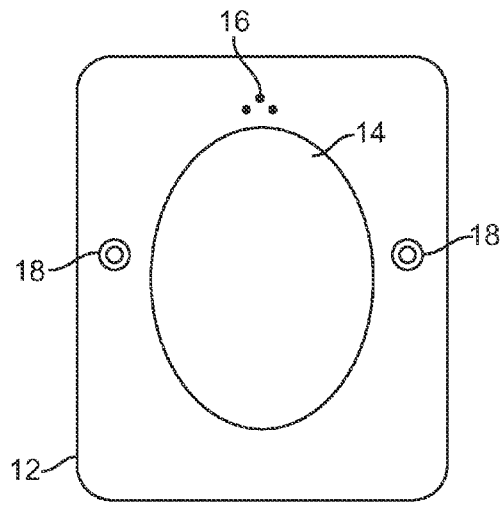
FIG. 3 is a front view of an alternative embodiment of a microphone used in the communication system of FIG. 1.
Figure 4:
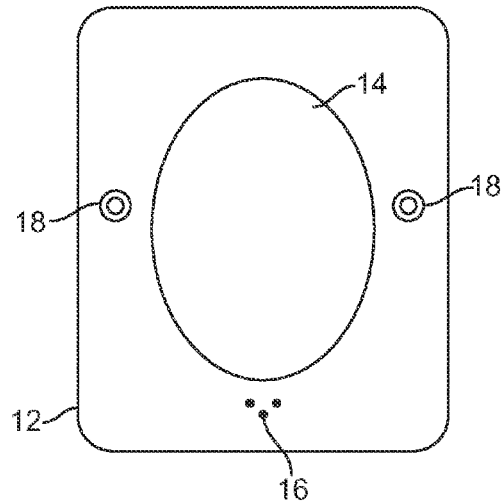
FIG. 4 is a front view of another alternative embodiment of a microphone used in the communication system of FIG. 1.

In an another embodiment, shown in FIG. 3, the microphone 16 is a bone-conductive microphone 16 that receives sound transmitted by the patient's bone(s) through the skin. Bone-conductive microphones are typically less sensitive to background noise and useful for receiving spoken signals. The bone-conductive microphone 16 is positioned in the cushion 12 to be adjacent the patient's forehead, as illustrated, or jaw, chin, or other bony structure, in order to pick up audible signals from the bony structure. In yet another embodiment, shown in FIG. 4, the microphone 16 is a throat microphone 16 for receiving tracheal sounds or other sounds directly from the patient's voicebox. The throat microphone 16 is optimally positioned in the cushion 12 to be in contact with the patient's neck for optimum reception of tracheal sounds.

Referring back to FIG. 1, the speakers 18 are positioned in the cushion 12 to deliver audible signals from the communication port 20 for the patient to hear and may be partially or fully embedded in the cushion 12. In the illustrated embodiment, the speakers 18 are embedded in the cushion 12, such that surfaces of the speakers 18 are substantially flush with an external surface of the cushion 12. In this manner, the speakers 18 are less likely to interfere with the patient's comfort, while still being sufficiently close for the patient to hear audible signals delivered through the speakers 18. The speakers 18 may include two or more speakers 18 positioned on opposing sides of the cushion 12, for example, adjacent the patient's ears when the patient's face is received in the opening 14. Music, noise, alarms, audio cues, etc. may be delivered to the patient via the speakers 18 to test for response, sooth the patient, wake the patient, keep the patient alert, or indicate to the patient a response is needed.

As discussed above, the communication port 20 receives the audible signals from the patient through the microphone 16 and delivers audible signals to the patient through the speakers 18. To this end, the communication port 20 may consist of any communication unit suited to the procedure, such as a computer (e.g., a laptop system), a radio unit, or a wireless communication center. Likewise, the communication port 20 may also utilize any communication technology suited for delivering and receiving audible signals, such as cables, or wireless technology such as Bluetooth®, Wi-Fi (e.g., 802.11x wireless LAN), RF telemetry, infrared, AM/FM, and/or pager bandwidth systems. A communication port (not shown), e.g., a radio unit, may be provided in or adjacent to the cushion 12 (e.g., on the operating room table) for transmitting signals between the communication port 20 and the microphone 16 and speakers 18. The communication port may be coupled to the microphone 16 and speakers 18 via signal cables.

The communication port 20 is in communication with one or more speaker elements 26 that allows medical personnel to receive the audible signals from the patient. For example, if the patient speaks into the microphone 16 to describe sensations experienced during the medical procedure, the patient's voice communication is delivered from the microphone 16 to the communication port 20, and in turn to the speaker element(s) 26, to be received by medical personnel. Examples of speaker elements include standing speakers, Bluetooth® devices, headphones, and/or one or more speakers built into the communication port 20. The communication port 20 may communicate with the speaker element(s) 26 through cables, radio signals, WiFi, Bluetooth® technology, or other suitable technologies. The speaker elements 26 may be directed towards the operating table or other target area. The directionality of the speaker elements 26 may be fixed or adjustable.

The communication port 20 is also in communication with one or more microphone elements 28, such that medical personnel may speak into the microphone element to communicate with the patient through the communication port 20 and speakers 18. For example, medical personnel may speak into the microphone element(s) 26 to ask how the patient is feeling or to convey other inquiries and/or instructions during a medical procedure. This communication from medical personnel is then delivered to the communication port 20 and in turn to the speakers 18 to be received by the patient. Examples of microphone elements include hand-held microphones, headsets worn by medical personnel, Bluetooth® devices, and one or more microphones built into the communication port 20. The communication port 20 may communicate with the microphone element(s) 28 through suitable technologies, such as those discussed above regarding the speaker element(s) 26.

In one embodiment, the communication system 10 is a half-duplex system that allows bi-directional communication between the patient and medical personnel through the communication port 20, wherein only one person is heard at one time. For example, while a doctor is delivering a message to the patient through the communication port 20 and the speakers 18, audible signals from the patient will not interrupt the communication through the speakers 18 from the doctor. This helps to ensure that the patient receives important communications from medical personnel during a medical procedure. Similarly, while a patient is speaking into the microphone 16, audible signals from medical personnel will not interrupt the communication through the microphone 16 from the patient. This helps to ensure that medical personnel receive important communications from the patient during a medical procedure. In yet another embodiment, the communication system 10 is a full-duplex system that allows simultaneous communication in both directions between the patient and medical personnel, such that communications from one of the patient or medical personnel do not interrupt the other and may be heard at the same time.

Priorities may also be assigned to microphones and speakers in the communication system 10. For example, the microphone element 28 may be assigned priority over the microphone 18 in the cushion 12, such that audible signals from the patient will not be heard when the microphone element 28 is in use, or vice-versa. As another example, the microphone 18 or microphone element 28 with priority may have audible signals delivered at a higher volume. For example, if two microphone elements 28 are used by medical personnel, one of the two microphone elements 28 may be assigned priority, such that if both microphone elements 28 are being spoken into at the same time, the patient will hear signals more loudly from the microphone element 28 with priority. The speaker elements 26 and microphone elements 28 can be intrinsic or mounted on a computer (e.g., laptop). Alternatively, or additionally, speaker elements and microphone elements can be provided to each member of the medical team via headsets. The communication port 20 may also be in communication with one or more display devices (not shown) for use by the medical team.

The communication port 20 may also include or be in communication with an automated device 30 that automatically provides audible signals, such as beeps or other cues, to be received by the communication port 20 and delivered to the patient. In one embodiment, the automated device 30 is a therapeutic system, such as a drug delivery or electrotherapy system. The communication port 20 receives operational indicators from the therapeutic system 30, e.g., stopping, starting, increasing, and/or decreasing therapeutic treatment. In turn, the communication port 20 delivers audible signals to the speakers 18 corresponding with the operational indicators. For example, upon receiving an operational indicator from the therapeutic system 30 that a particular therapy is about to begin, the communication port 20 delivers a series of beeps or other audible signal to the speakers 18. This may benefit the patient by keeping the patient informed about the status of a medical procedure, thus helping the patient to be aware of ongoing procedures and also to be more at ease with the procedures. Additionally, this may also prompt the patient to respond with audible signals through the microphone 16 to medical personnel. For example, upon hearing a beep through the speakers 18 that a therapeutic process has begun, the patient may respond about any sensations experienced from the therapeutic process, or whether the patient is experiencing any pain. To this end, the communication port 20 may be programmed to recognize operational indicators from the automated device 30 for sending pre-selected audible signals to the speakers 18 corresponding to such indicators.

The channel between the patient communication port and the medical team communication port 20 may be encoded to prevent static and/or interference from other frequencies, or, to allow private interactions between medical team members and/or between a specific medical team member and the patient. Multiple channels and/or a multiplexer may also be used to allow multiple medical team members to switch between communication with the patient and with other team members. For example, the physician may wish to only speak with one other team member (e.g., the anesthesiologist).

The communication system 10 includes a display device 32 for the patient to view during a medical procedure that displays selected areas of the patient's body. In the illustrated embodiment, the display device 32 is hung underneath the operating room table, and specifically, underneath the opening 14, so that it may be easily viewed by the patient. The display device 32 may be secured by magnets, screws, adhesive, or other means attached to string cables, or wires, such that the display device hangs under the operating table. The display device 32 may be programmed to show selected areas of the patient's body (e.g., area(s) of the patient's body that may feel paresthesia and/or pain (e.g., the head)) The areas may be divided into sections that may be numbered, colored, or labeled by other means. The display device 32 may allow the patient to dictate where they feel sensations, such as paresthesia and/or pain. In an optional embodiment, a speech recognition program may recognize, display, and record interactions between the patient and the medical team. For example, the program may recognize the label of a section the patient responds to and the display device 32 may either display the label (e.g., a number) or highlight that section on the display device 32 (and/or the display device used by the medical team).

The display device 32 may allow both the patient and medical team to interact effectively and specifically in reference to where the patient feels paresthesia and/or pain. Optionally, the display device 32 may take the form of virtual reality or video glasses that may allow the patient to see where the physician is palpating and may show the same labeled areas discussed above. The display device 32 may receive signals from the automated device 30. As one example, the display device 22 automatically generates a display showing a section of the patient's body based on communication from the automated device 30 (e.g., the therapeutic system) that treatment is about to begin in that section. The display device 32 may also display selected areas of the patient's body based on direct input from medical personnel and/or the patient, for example, by voice commands delivered through the communication port 20 or directly to the display device 32, or from a computer unit included in the display device 32.

The display device 32 is preferably positioned for easy viewing by the patient and can be separate from the cushion 12, or integrated with the cushion 12, as illustrated in FIG. 1. Thus, the patient may view areas being treated during the medical procedure while providing and receiving audible signals through the microphone 16 and the speakers 18, respectively, to facilitate the procedure.

The display device 32 may optionally be in communication with one or more sensation generators (not shown) that deliver sensations to the patient suited to the medical procedure. For example, a series or matrix of sensation generators may be placed on the surface of the patient's skin, which may produce pressure (e.g., stimulated touch), vibration, or stimulation sensations (e.g., using Transcutaneous Electrical Neural Stimulation (TENS) electrodes). The sensation generators may be attached to the patient individually or they may be all attached to a device (e.g., a skull cap), which is then placed on the patient. The sensation generators may be turned on individually or in groups. The sensation generators may be activated remotely, via manual input (e.g., buttons or switches), or using special gloves with embedded sensors (e.g., strain gauges, piezoelectrics, etc.) where moving a specific finger turns on a specific sensation generator or group of sensation generators.

The sensation generators may serve as reference points for the patient by simulating when the physician touches an area of the body with a finger, and the display device 32 (and/or a display device for use by the medical team) may show the location of these sensation generators for reference. Upon activation of specific sensation generators, the patient may indicate which labeled sections correlate to paresthesia sensations. For example, if a sensation generator delivers a sensation to a portion of the patient's leg, the patient may view on the display device 32 an image of the patient's leg with a visual cue (e.g., a dot or other marker) indicating that sensation is presently being generated to that portion of the patient's leg. The physician may then ask "Do you feel paresthesia here?". The patient may then communicate through the microphone 16 whether the patient feels any sensation in the leg from the sensation generator, or how the sensation feels. This may be helpful during paresthesia from neurostimulation or during muscle stimulation and/or other types of physical therapy. The markers for the sensation generators may remain for reference after the sensation generators have been removed from the patient.

Another specific type of sensation generator may use an RF beacon, which in reality, does not produce sensation, but may be placed on the patient and used in the same way as the generators described above. A sterile pen, as part of the sensation generator, carries an RF marker that is used in conjunction with these beacons. The physician may move the pen in contact with the area covered by the beacon "matrix" and an location determination algorithm may calculate the location of the pen on the area of the body. This location may then be shown on the display device 32 (and/or the display device(s) used by the medical team. Therefore, the patient can both feel where the physician is touching them with the pen and visualize where the pen is on the display device 32.

The communication port 20 includes a recorder 34 for recording audible signals delivered through the communication port 20. The audible signals recorded on the recorder 21 may be maintained for the patient's records, reviewed for diagnostic or research purposes, or other uses.

Having described the components of the communication system 10, a method of using the communication system 10 will now be described. First, a patient is prepared for a medical procedure, as required by the procedure. Next, referring to FIG. 5, the patient is positioned for the procedure by placing his/her face in the opening 14 in the cushion 12, and in particular, by placing the patient's face in the opening 14. In this manner, the patient's mouth is positioned near the microphone 16 to enhance the clarity of the patient's audible signals delivered to the communication port 20. The patient's ears are also positioned near the speakers 18 to enhance the clarity with which the patient hears audible signals delivered by the communication port 20, such as audible signals from medical personnel and/or the automated device 30. Because the microphone 16 and speakers 18 are at least partially embedded in the cushion 12, the microphone 16 and speakers 18 impart minimal, if any, discomfort to the patient.

Figure 5:
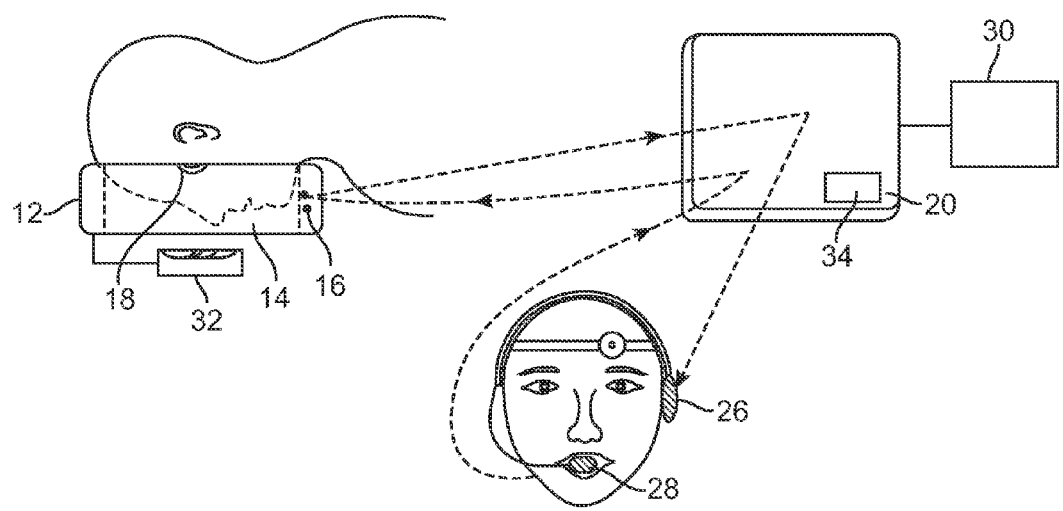
FIG. 5 is a plan view of a method of using the communication system of FIG. 1 with a patient.

After the patient is positioned in the cushion 12, the medical personnel begin performing the medical procedure. During the medical procedure, the patient submits audible signals to the microphone 16 to communicate with medical personnel as desired or as directed by the medical personnel. For example, in the embodiment in which the microphone 18 is positioned near the patient's mouth, the microphone 18 receives voice communications from the patient that are delivered to medical personnel via the speaker element 26 and the communication port 20. In FIG. 5, the speaker element 26 is illustrated as a headset combining both the speaker element 26 and the microphone element 28. The medical personnel then use the patient's audible signals to determine the patient's status, the effectiveness of the procedure, the comfort level of the patient, or other information that can be used to optimize the medical procedure.

Alternatively, in the embodiment in which the microphone is a bone-conductive microphone 18, the microphone 18 is positioned near a bony structure of the patient and receives audible signals from the bony structure that are delivered via the communication port 20 to medical personnel as described above. In the embodiment in which the microphone 18 is a tracheal microphone 18, the microphone 18 is positioned adjacent the patient's neck and receives audible signals from the patient's voicebox that are delivered via the communication port 20 to medical personnel as described above.

The patient also hears instructions or other information regarding the procedure delivered by the communication port 20 through the speakers 18. As an example, during the procedure, the medical personnel speak through the microphone element 28, and these audible signals are delivered to the patient via the speakers 18 and the communication port 20. In this manner, the patient can be informed of the status of the procedure, receive an inquiry from the medical personnel to which the patient can respond, or be apprised of other information that enhances the patient's ease during the procedure or helps in optimizing the procedure as it is performed by medical personnel.

The patient may also receive audible signals from the automated device 30 that are delivered via the communication port 20. As an example, during the procedure, the automated device 30 sends an operational indicator to the communication port 20 that a type of therapy is about to be administered. In turn, the communication port 20 recognizes the indicator and sends a corresponding audible signal, such as a series of beeps, to the speakers 18 to prepare the patient for the therapy.

In the embodiment including the display device 32, the patient views the display device 32 during the medical procedure to be aware of the status of the medical procedure and/or to provide input regarding the procedure. For example, the patient may receive an audible signal through the speakers 18 that the patient's lower back is about to receive an anesthesia. The patient may then view the lower back on the display device 32 as the lower back is touched by medical personnel and speak into the microphone 16 to indicate whether the patient is experiencing any sensation in the areas touched. As another example, in the embodiment in which the display device 32 communicates with sensation generators, the patient views parts of the body receiving sensation on the display device 32, and then communicates through the microphone 16 to indicate what sensations the patient is experiencing.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A cushion-mounted patient communication system, comprising: a cushion having an opening for receiving the patient's face; a microphone at least partially embedded in the cushion for receiving audible signals from the patient when the patient's face is received within the opening; a programmable display device integrated with the cushion and viewable by the patient when the patient's face is received within the opening, wherein the programmable display device is configured for displaying selected areas of the patient's body other than the head and face; and at least one speaker at least partially embedded in the cushion for delivering audible signals from an operator to the patient when the patient's face is received within the opening.

2. The communication system of claim 1, further comprising an external communication port for receiving the patient's audible signals from the microphone and for delivering the operator's audible signals to the speaker.

3. The communication system of claim 2, wherein the communication port is configured for receiving the patient's audible signals from the microphone and for delivering the operator's audible signals to the speaker via wireless communication.

4. The communication system of claim 1, wherein the microphone is a bone-conductive microphone.

5. The communication system of claim 1, wherein the microphone is a throat microphone.

6. The communication system of claim 1, wherein the microphone is configured for being positioned adjacent a mouth of the patient when the patient's face is received within the opening.

7. The communication system of claim 1, wherein the at least one speaker comprises a plurality of speakers positioned on opposing sides of the cushion, the speakers configured for being positioned adjacent to the ears of the patient when the patient's face is received within the opening.

8. The communication system of claim 1, wherein the at least one speaker is substantially flush with an external surface of the cushion.

9. The communication system of claim 1, wherein the microphone is substantially flush with an external surface of the cushion.

10. The communication system of claim 1, wherein the communication system is a half-duplex system for allowing bi-directional audible communication between two or more persons, wherein only one person is heard at one time.

11. The communication system of claim 1, wherein the cushion comprises two separate portions joined by connecting elements at substantially opposite ends of the separate portions, and the width of the opening is adjustable by sliding at least one of the two separate portions along the connecting elements.

12. The communication system of claim 1, wherein the cushion has a shape selected from a ring, horseshoe, and rectangle.

13. A method for a patient to communicate during a medical procedure, comprising: positioning the patient's face in an opening surrounded by a cushion, wherein the cushion supports the patient's head; delivering first audible signals from the patient into a microphone at least partially embedded in the cushion, wherein the first audible signals are delivered to a communication port; delivering second audible signals to the patient from the communication port through at least one speaker that is at least partially embedded in the cushion; displaying selected parts of the patient's body other than the head and face at a programmable display device integrated with the cushion, wherein the programmable display device is viewable by the patient when the patient's face is positioned within the opening; and performing the medical procedure on the patient while the patient's face is positioned in the opening.

14. The method of claim 13, further comprising receiving commands from the communication port to display the selected parts of the patient's body at the display device.

15. The method of claim 13, further comprising recording the first and second audible signals at the communication port.

16. The method of claim 13, wherein the first audible signals are delivered to the microphone via a bone of the patient.

17. The method of claim 13, wherein the first audible signals are delivered to the microphone via the trachea of the patient.

18. The method of claim 13, further comprising wirelessly communicating the first and second audible signals between the microphone and at least one speaker and the communication port.

* * * * *